United States Patent [19]

Jacob

[11] 4,226,906

[45] Oct. 7, 1980

[54] MICROPOROUS COATED FABRICS FROM CLUSTERED MICROSPHERES

[75] Inventor: Ezekiel J. Jacob, Brooklyn, N.Y.

[73] Assignee: John Brian Haworth, Westport, Conn.

[21] Appl. No.: 933,541

[22] Filed: Aug. 14, 1978

[51] Int. Cl.³ .................. B32B 5/16; B32B 27/14
[52] U.S. Cl. .................. 428/283; 428/290; 428/306; 428/308; 428/404; 428/406; 428/407
[58] Field of Search .......... 428/304, 306, 308, 310, 428/315, 68, 80, 403, 404, 406, 407, 240, 241, 262, 267, 283, 290

[56] References Cited

U.S. PATENT DOCUMENTS

| | | | |
|---|---|---|---|
| 2,806,509 | 9/1957 | Bozzacco et al. | 428/241 |
| 3,353,981 | 11/1967 | Jacob | 428/262 |
| 3,429,955 | 2/1969 | Johnson et al. | 428/406 |
| 3,718,561 | 2/1973 | Jacob | 204/130 |
| 3,917,547 | 11/1975 | Massey | 428/310 |
| 3,930,088 | 12/1975 | Constantin et al. | 428/240 |
| 3,993,608 | 11/1976 | Wells | 428/310 |
| 3,996,654 | 12/1976 | Johnson | 428/315 |
| 4,018,962 | 4/1977 | Pedlow | 428/310 |

*Primary Examiner*—William J. Van Balen
*Attorney, Agent, or Firm*—Kenyon & Kenyon

[57] ABSTRACT

Poromeric plastic coated fabrics containing embedded therein microspheres disposed in natural or synthetic clustered domains each constituted by a matrix insoluble in the coating composition, the clustered domains adjacent to one another but spatially separated horizontally and vertically to provide substantially uniform microporosity throughout the coating.

10 Claims, 10 Drawing Figures

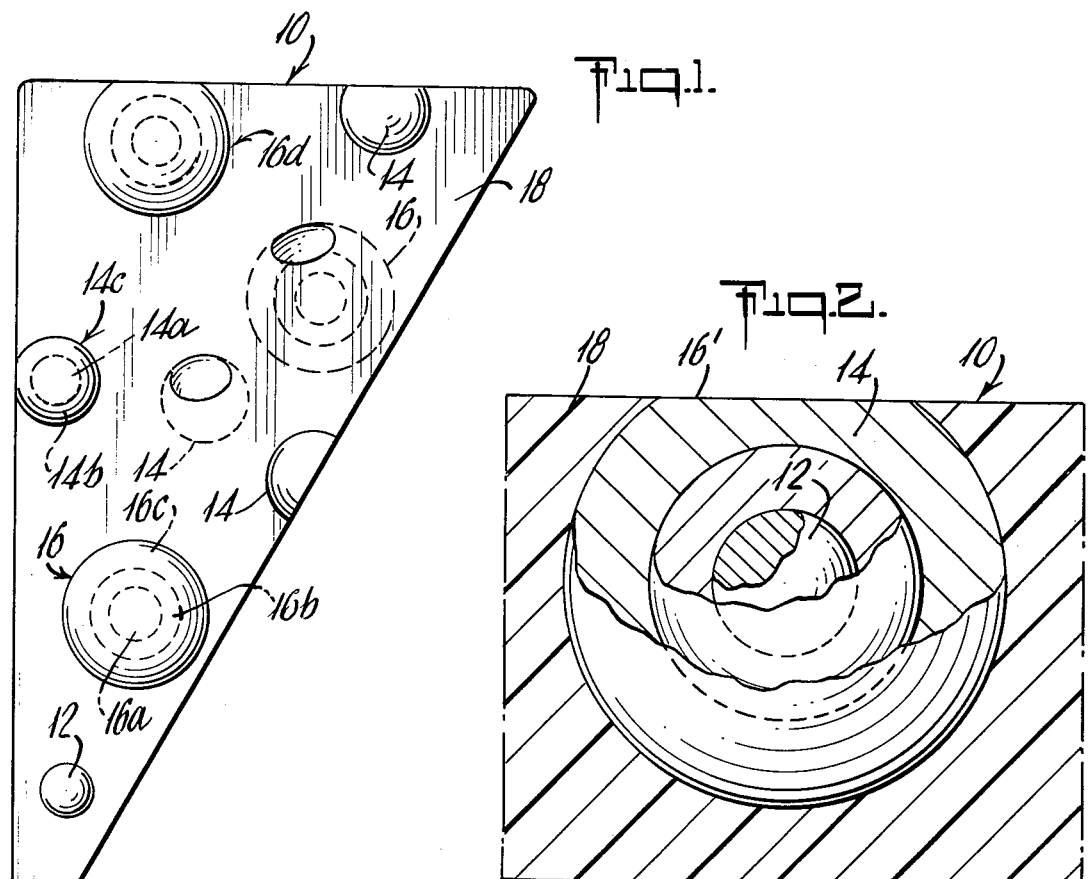
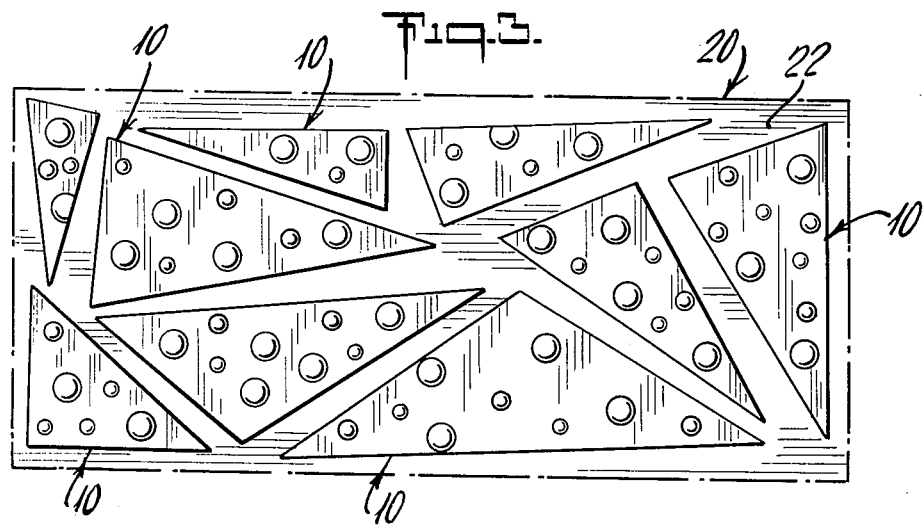

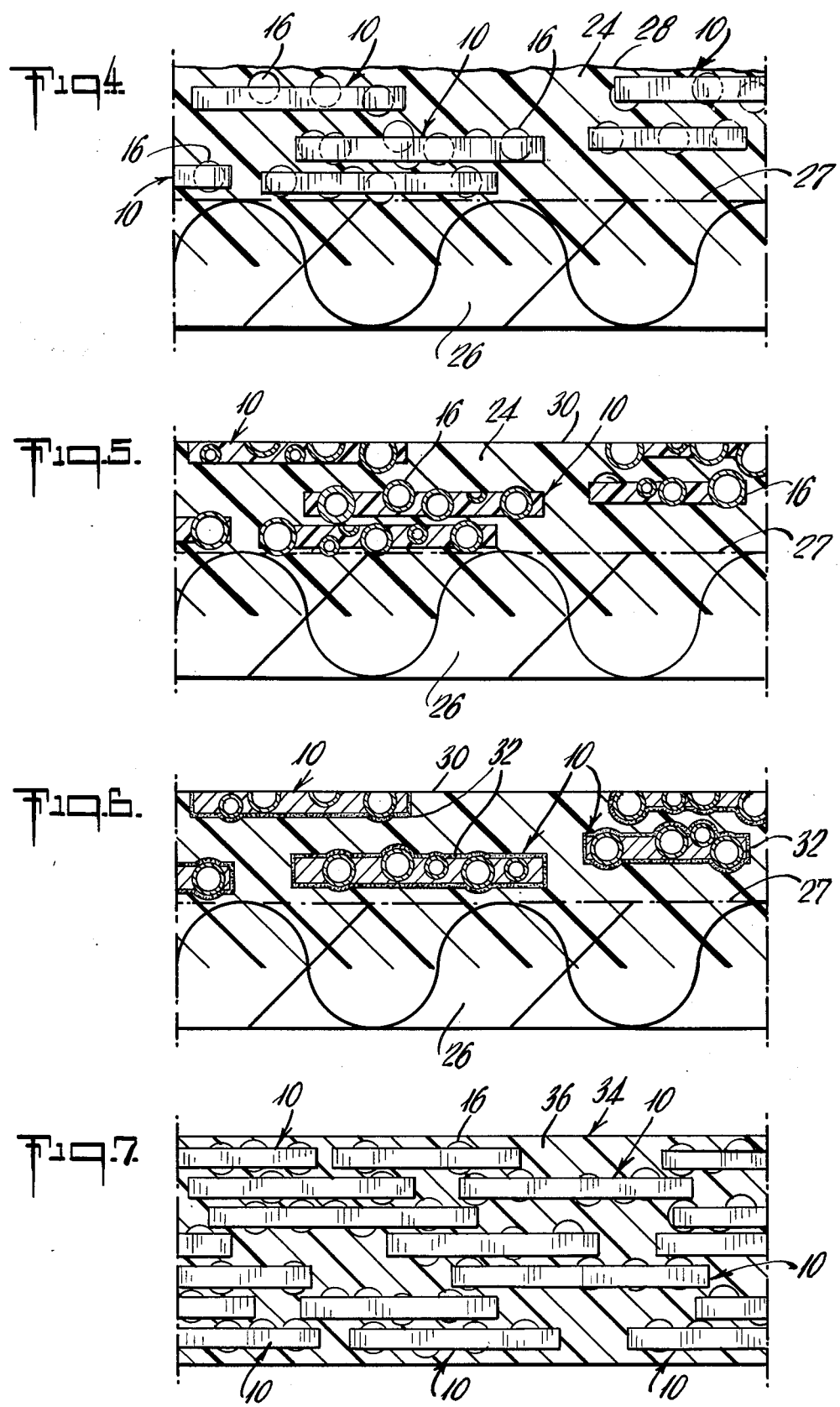

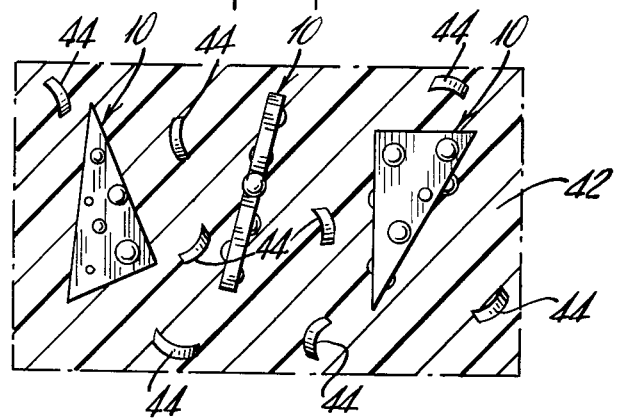
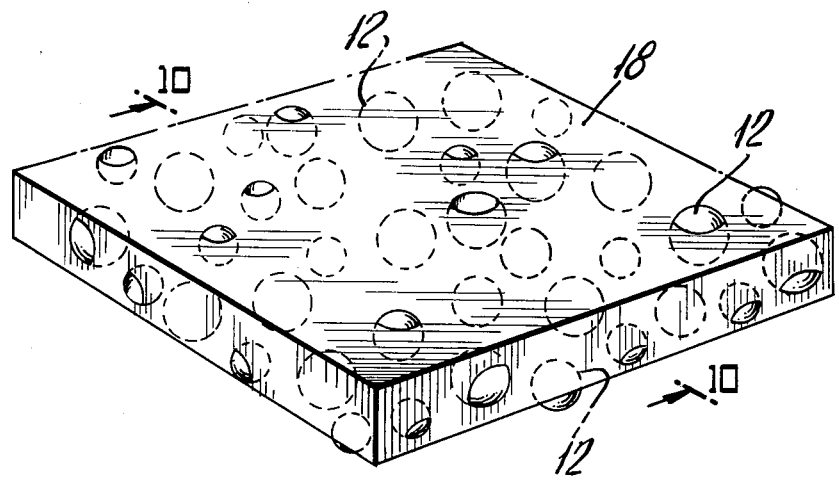
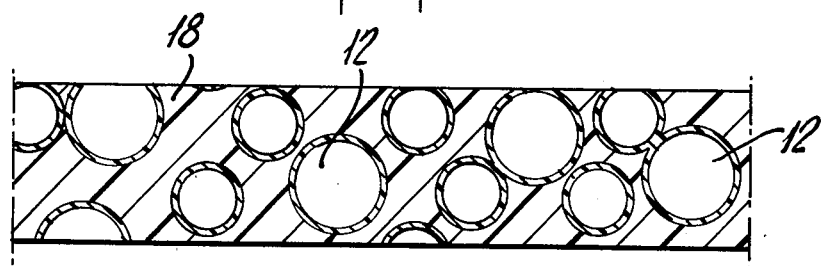

MICROPOROUS COATED FABRICS FROM CLUSTERED MICROSPHERES

BACKGROUND OF THE INVENTION

Poromeric plastic coated fabrics were known in the prior art. Such materials as "Corfam" of duPont, "Aztran" of B. F. Goodrich, and "Genaire" of General Tire Company have been or were on the market for several years, each with dubious success and ultimate failure. The plastic coated fabrics may be made in a variety of ways, e.g., with polyvinyl chloride, polyurethane and the like polymers, and the microporosity being provided with various means including single microspheres as disclosed in my prior U.S. Pat. Nos. 3,353,981 and 3,718,561, as well as in my simultaneously filed U.S. Pat. application Ser. No. 933,543, filed Aug. 14, 1978. A disclosure of the invention of the present application was made in summary form in Disclosure Document No. 071468 dated May 23, 1978.

The use of single microspheres, in production, sometimes tends to give erratic results, and an end product which lacks uniformity throughout its area as regards microporosity. It also may lack, unpredictably, cosmetic elegance due to the tendency of single microspheres to move towards each other and cluster in random fashion in the coating material while the coating material is still fluid.

BRIEF SUMMARY OF THE INVENTION

According to the present invention, I use clustered microspheres which move in clustered domains while motile in the fluid coating menstruum. Upon solidification, the domains, which have moved towards each other during solidification of the coating will contain the individual microspheres spatially disposed towards each other in their pristine form, even though the domains may have moved according to the process of this invention. The clustered microspheres may be of synthetic resin such as the microspheres of U.S. Pat. No. 3,353,981. These clusters are prepared by bonding individual microspheres into a bonding matrix which is insoluble in the coating composition and will retain the matrix-contained microspheres in their original spaced pattern. Thus the bonding agent for the matrix could be a polyvinyl alcohol which is water soluble but not soluble in a polyvinyl chloride coating composition consisting of a solvent solution of the P.V.C. resin or a plasticizer-dispersion of the P.V.C. resin as in the plastisol coating technology. Clustered microspheres are preferred in the form of high melting thermoplastic (glass) microspheres which occur naturally as clusters.

The naturally occurring material is composed of spherulitic aggregates of porphyritic rhyolite, a vitreous white rock form of aluminum silicate containing within its mass, a countless number of infinitesimal gas bubbles trapped in rapidly cooling lava during the primeval formation of the material, each bubble encased in a hard vitreous shell.

DESCRIPTION OF THE DRAWINGS

FIG. 1 is an enlarged plan view of a single domain of a microsphere cluster;

FIG. 2 is an enlarged sectional plan view of a cluster of three concentric microspheres;

FIG. 3 is a schematic sectional plan view of a plurality of microsphere clusters disposed in a coating composition;

FIG. 4 is an enlarged end elevation of a coated fabric;

FIG. 5 is an enlarged elevation in section of a coated fabric;

FIG. 6 is an enlarged elevation in section of a coated fabric in which the individual domains are separately coated;

FIG. 7 is an end elevation of a coating or a film in which the domains are distributed in vertically separated lamellae;

FIG. 8 is a plan view of a brake lining made of the material of the present invention;

FIG. 9 is an isometric view of a synthetic clustered microsphere domain; and

FIG. 10 is a vertical section taken along lines 10—10 of FIG. 9.

DETAILED DESCRIPTION

Referring now to the drawings and particularly FIG. 1, a single representative clustered domain or aggregated particle is shown and designated generally by reference numeral 10. It is comprised of single microspheres 12 (one shown), a plurality of double microspheres 14 constituted by a smaller microsphere 14a encapsulated within a larger, outer concentric microsphere 14b, and a plurality of triple microspheres 16 constituted by three layers 16a, 16b and 16c of concentric microspheres, all such microspheres embedded either partially or completely in a binder material. Some of the microspheres such as 14c, 16d are partially sectioned and exposed at the surface 18 of the domain. As will be described in more detail below in describing the methods of preparation, the naturally occurring domain is comprised of vitreous microspheres embedded in a predominantly siliceous matrix, e.g., aluminum silicate, and the synthesized domain is comprised of glass microspheres disposed in a polymerized resin, e.g., polyvinyl alcohol, or any other suitable matrix that is insoluble in the coating medium into which the domains are to be ultimately dispersed. The generally triangular form of the particle shown is characteristic of the naturally occurring particle when subjected to mechanical size reduction.

FIG. 2 shows in enlarged detail a cluster of three concentric microspheres wherein there is an innermost microsphere 12, an intermediate layer 14 and an outer layer 16. The view is partially sectioned to show that each layer constitutes a separate and distinct microsphere.

FIG. 3 is a generalized plan view of a plurality of domains 10 disposed in a coating composition or plastic matrix 22, e.g., polyvinyl chloride (hereinafter sometimes PVC) constituting an article of manufacture 20.

FIG. 4 depicts a partial cross-section of a fabric coated with a plastic film made in accordance with the principles of the present invention. Individual domains 10, natural or synthetic, are disposed in randomly spaced positions in plastic matrix 24 which is coated upon and adhered to any suitable fabric 26. In the embodiment shown, the outer surface 28 of the matrix 24 is continuous, i.e., no domains 10 are exposed. Triple concentric microspheres 16 are shown in random disposition. Furthermore, the respective domains 10 have their elongated axes generally aligned in horizontal planes generally parallel to one another and to the fabric-plastic interface 27. Such alignment is the natural consequence of the method of manufacture of the composition and in situ coating of the fabric as described below.

FIG. 5 is a complete cross-section of the coated fabric of FIG. 4 showing distribution of single, double and triple microspheres 12, 14 and 16, respectively, in section. Some domains 10 are exposed on surface 30.

FIG. 6 shows an optional modification of the domains 10, each of which is encased within coating 32 which is chemically different from, an insoluble in, plastic coating composition 24. Coating 32 may be, for example, carboxy methyl cellulose or melamine formaldehyde.

FIG. 7 shows a further modification involving a relatively thick lamellar coating 34 in which a plurality of domains 10 are disposed in coating composition 36 by building up successive layers, one at a time, or by extruding composition 36 as a self-sustaining film wherein the domains 10 emerge packed upon each other as multi-level layers.

FIG. 8 is a schematic plan view of a representative portion of a brake lining containing the composite structure of the present invention in which plastic resin matrix 42 contains randomly distributed domains 10 in the form of triangular wafers and interspersed metal chips 44 which act during use of the brake lining material as particulate heat sinks by virtue of their having a higher specific heat than that of the domains 10 or binder material 42.

The preferred compositions and/or methods of preparation of the domain containing, matrices in accordance with the principles are as follows.

BRAKELINING MATERIAL

Triangular wafers 10 are disposed in many planes with axes randomly oriented at many angles and held in a matrix 42. Matrix 42 is a cured phenol-formaldehyde resin. Metal chips 44, e.g., brass chips, are disposed within the matrix to act as heat-sinks.

Typical formula for an automotive brake lining:

| | |
|---|---|
| Matrix, thermoset heat-resisting resin: | 24 parts by weight |
| Clustered microspheres: | 54 parts by weight |
| Brass chips: | 20 parts by weight |
| Friction modifiers, e.g., Cardolite sold by 3M: | 2 parts by weight |

Typical formula for a non-automotive friction element suitable for electric motors, clutch facings, etc.:

| | |
|---|---|
| Matrix, thermoplastic high heat-resistant resin polysulfone: | 44 parts by weight |
| Clustered microspheres (325 U.S. Standard mesh): | 54 parts by weight |
| Friction modifiers: | 2 parts by weight |

For a high traction Vee belt resistant to glazing: the cord is first treated with a dip composed of:

| | |
|---|---|
| Resorcinol formaldehyde: | 100 parts by weight |
| Clustered microspheres | 3 parts by weight |

The cord is then laid in an uncured rubber binder having the usual curatives in it. Thus Neoprene will have MgO, Sb$_2$O$_3$ or will have sulfur and accelerators. A typical formula for the belt compound:

| | |
|---|---|
| Belt rubber compound, uncured: | 100 parts by weight |

| | |
|---|---|
| -continued | |
| Clustered microspheres: | 10 parts by weight |

After incorporation is complete, the rubber compound is molded and cured with the cords laid in it. The finished belt is highly resistant to glazing and loss of friction caused by glazing. The clustered microspheres expose fresh microspheres with their cup-like action to renew and raise the coefficient of friction. The broken microsphere walls fall away and exert a mildly abrasive scavenging action on the driving and driven members.

In automotive brake linings the formula given above in which the clustered microspheres essentially have replaced asbestos, the advantage gained by the freshly exposed microspheres is apparent by the absence of "fade" as compared with the asbestos control.

| Breathable Coated Fabric | |
|---|---|
| Part 1 | |
| Polyvinyl Chloride Plastisol | lbs. |
| Polyvinyl chloride resin diamond VF 71 | 100 |
| Dioctyl Phthalate | 35 |
| Black in DOP - Carbon black dispersion 15% pigment | 10.00 |
| Didecyl Phthalate | 10 |
| Di iso octyl Adipate | 5 |
| Epoxy plasticizer Drapex 4.4 (argus Chem. Co., Brooklyn, N.Y.) | 5 |
| Santicizer 711 (Monsanto Chem. Co., St. Louis, Mo.) | 5 |
| Stabilizer (Barium-Cadmium base) Argus Mark KCB | 3 |
| De aerator, polyethylene glycol 400 monolaurate | 3 |
| Coupler - natural oil of sweet almonds USP | 0.5 |

Mix all liquids then slowly add the PVC resins until dispersed.

| Part 2 | |
|---|---|
| Slurry of Clustered Microspheres | lbs. |
| Clustered microspheres | 100 |
| Water | 100 |

Mix well until slurried.

| Part 3 | |
|---|---|
| Mobility Extender for Clustered Microspheres | lbs. |
| Carboxy methyl cellulose High viscosity duPont P 75 FS H (carboxymethyl cellulose) or equivalent | 3 |
| Water | 100 |

Mix well until dissolved.

| Part 4 | |
|---|---|
| Mother Liquor Containing Clustered Microspheres | lbs. |
| Part 3 | 75 |
| Part 2 | 25 |
| Breathable Vinyl Formula | lbs. |
| Part 1 (Plastisol) | 100 |
| Part 4 mother liquor with clustered microspheres | 5 |

Incorporate together by mixing.

COATING PROCEDURE

Use casting paper such as S.D. Warren Vinyl Casting paper such as "Hi Calf EHR".

Lay down a wet coating of breathable vinyl formula about 0.010".
Cure in oven at 300° F. for 3'.
Allow to cool. This is called the "skin".
Now lay down a second wet coat 0.008".
While coating is wet apply and laminate a layer of suitable fabric. This is the adhesive coat. In this case as an example, use a non-woven polyester fabric sold by Burlington Industries under the trade name of "Nexus". When the fabric has been adhered, cure in oven at 300° F. for 3½' min. then cool. Strip the coated fabric from the casting paper. It is now a microporous poromeric fabric. It is freely "breathable". MVT (Moisture Vapor Transmission) is the upper limit of the ASTM test using a Thwing Albert Vapometer. Test is described in U.S. Pat. No. 3,718,561 and ASTM. The breathable fabric is used for shoe linings.

UPHOLSTERY FORMULA

Prepare the skin as in the previous example. Apply thereon a second skin coat and cure in the same way. Now run through a wringer. Apply an adhesive coat and wet-laminate thereon a layer of heavy knitted material. A 3.2 oz. cotton jersey "Knitback" is preferred.
Cure at 350° F. for 3'.
The thickness is 0.030".
The upholstery material has an MVT of 17 grams per square meter per hour and is air permeable. ASTM flex test exceed 50,000 cycles. The clustered microspheres have introduced additionally a new dimension of comfort in all the poromeric produced therefrom, including the upholstery, the shoe lining, shoe upper, outer wear, etc., namely absorption. Earlier poromerics did not have absorption. Absorption contributes to comfort.

SHOE UPPERS, LADIES

Repeat the procedure and the formula in "Upholstery Formula" above with these changes:
Increase wet thickness of adhesive coat from 0.008" to 0.010".
For fabric use 5 oz. napped cotton sateen.
The thickness of the finished poromeric ladies shoe upper material is 0.033"–0.035".

SHOE UPPERS, MEN

Repeat upholstery formula with the following changes and modifications:
Increase wet thickness of each and every skin layer by 0.002".
Apply a third skin layer of 0.012".
Squeeze through a wringer when cool.
For final adhesive layer increase adhesive to 0.013".
For fabric use polyester cotton, e.g., a 50—50 blend.
For curing, cure at 350° F. for 3½'.
The finished thickness of the clustered microspheres-based shoe upper mens, is 0.065".
It is freely breathable and absorbent. A pair of shoes will admit water into the shoe at the welt, so great is the comfort factor, equal in fact to glove leather. This condition is overcome in my copending application entitled "Poromeric Shoe with Selectively De-poromerized Sections" where the poromeric material is de-poromerized in the area nearest to the welt, thus excluding the passage of water and increasing the flex-life and abrasion resistance in the desired area.

| Calendered PVC | lbs. |
|---|---|
| PVC Resin Geon 101 PVC, calendering grade | 50 |
| PVC Resin Geon 103 EP, calendering grade | 50 |
| DOP | 50 |
| Drapex 4.4 (Argus) - i.e., epoxidized oil | 4 |
| Di iso octyl adipate | 4 |
| Stabilizer mark KCB (Argus) - i.e., a barium-cadmium laurate (a metathenic soap) | 2 |
| Stearic acid | 0.5 |
| Clustered microspheres | 20.0 |
| Mix on a two roll mill at 330° F. | |
| Calender on 3 roll calender. | |
| Roll heat as follows: | |
| 310 = top of roll | |
| 320 = middle roll | |
| 325 = bottom roll | |

Calender to 0.004" speed 100' per minute. Film is leak proof with a Mullen Hydrostatic of ½ yet it has moisture vapor transmission of 0.1. Control without clustered microspheres has an MVT of zero.

EXTRUDED POLYETHYLENE FILM

Illustrates orientation in layered fashion perpendicular to the force applied in the extrusion die.
Breathable polyethylene film is needed for disposable diapers. Plastic film currently used has zero MVT, and this tends to cause diaper rash in infants.

| | lbs. |
|---|---|
| Film grade polyethylene | 100 |
| 325 mesh or finer clustered microsphere domains | 20 |

The film is extruded to 0.001". It has an MVT of 0.1 yet is leak proof. Increasing the clustered microspheres will increase the MVT at some sacrifice of mechanical strength. The fine 1000 mesh clustered microspheres give better results due to large surface area and relatively greater numbers of ruptured microspheres in each of the clusters.

BREATHABLE POLYURETHANE POROMERIC

This is suitable for wearing apparel and outwear. It resists dry cleaning whereas the polyvinyl chloride based poromeric does not.

| Formula: Part 1 | lbs. |
|---|---|
| Estane 5702 BFG | 25 |
| Dimethyl Formamide | 5 |
| Methyl ethyl ketone | 95 |
| Titanium dioxide | 5 |
| Dow Corning silicone fluid 200 | 5 |
| Dimethyl siloxane 200 cps. viscosity sold by Dow Corning Corp., Midland, Mich. | |

| Part 2 | |
|---|---|
| Mother liquor containing clustered microspheres from breathable coated fabric example, supra. | 5 lbs. |
| Mix Part 2 into Part 1. | |

Cast coat exactly as above described for shoe lining with the following changes:
Cure of skin coat is carried at 230° F.

Cure of the finished laminate is carried out at 250° F. Fabric is 2 ounce Rip-Stoa nylon, parachute cloth.

| Non-Staining Polyurethane Poromeric Formula | |
|---|---|
| Skin Coat - Formulation: | lbs. |
| Bayer 213 aliphatic polyurethane solution 25% solids in Toluene - Isopropanol | 100 |
| Dow Corning 200 Dimethyl siloxane | 1 |
| $TiO_2$ solids from a polyurethane solution | 10 |
| Clustered microsphere Mother liquor from breathable coated fabric example, supra - page 9 | 3 |
| Mix mother liquor into polyurethane solutions. | |

| Adhesive Coat Formulation: | lbs. |
|---|---|
| Bayer 214 Aromatic polyurethane clear solution (25% solids) | 100 |
| Clustered microsphere mother liquor | 3 |

Mix the mother liquor into the polyurethane solution. Coating procedures exactly as in previous procedure for breathable polyurethane poromeric except that the fabric is a 4 ounce white napped fine denier nylon. The smooth side is to be laminated. Adhesive coat is cut down to 0.004". The coated fabric is poromeric highly breathable and comfortable. As a raincoat material, it is shower resistant, but it is not storm proof. Rain leaks through the shoulder areas. To overcome this yet retain the extraordinary comfort and breathability, selective areas in the shoulder region are de-poromerized according to the teachings of my copending application Ser. No.

TENT FABRIC

Formula used is exactly as in the poromeric shoe lining with these changes:

Add 5 lbs. of $Sb_2O_3$ into both the skin and the adhesive coating formulations. Eliminate 35 lbs. DOP and substitute in its place TriCresyl phosphate. Add 1 lb. Irganox 1010 [Ciba anti-oxidant (hindered phenol)].

Fabric used is 8 oz. nylon Duck.

The coating is highly breathable, allows condensation within the tent to be transmitted through and way into the outside. The poromeric tent is selectively de-poromerized in the topmost section and in the region of the tent adjacent to areas of attachment according to my copending application Ser. No.

The naturally occuring rhyolite is a complex aluminum silicate containing minor amounts of silica with some potassium, sodium and other trace amounts of other chemicals.

Typical chemical composition of rhyolite is as follows:

| | Weight % |
|---|---|
| Silica ($SiO_2$) | 73.20 |
| Aluminum Oxide ($Al_2O_3$) | 19.00 |
| Magnesium Oxide (MgO) | .11 |
| Iron ($Fe_2O_3$) | .40 |
| Calcium (CaO) | .32 |
| Potassium ($K_2O$) | 1.50 |
| Sodium ($Na_2O$) | 1.50 |
| L.O.I. (1000° C. | 3.90 |

Metals listed are complexed in the mineral structure and do not exist as free oxides.

Typical physical properties of the naturally occurring rhyolite are as follows:

| | |
|---|---|
| Dry Density: | Pounds of product per cubic foot. |
| | 200 Mesh = 45 to 37 lbs/cu. ft. |
| | 325 Mesh = 30 to 33 lbs/cu. ft. |
| | Fines = 29 lbs/cu. ft. |
| Wet Bulking Value: | Gallons per pound of product. |
| | .048 galls per pounds = 4.8 gallons per 100 pounds. |
| Wet Bulk Density: | 20.8 lbs. per gallon of product. |
| Oil Absorption Tests: | Using the Spatula rub out method, the ASTMA D-281, (lbs. of oil per 100 lbs. of Product 76) |
| | 200 Mesh = 32 to 36 lbs. |
| | 325 Mesh = 39 to 43 lbs. |
| | Fines 32 = 40 to 42 lbs. |
| Water Absorption: | Using twenty-four hour wetting period Ml $H_2O$ per gram of Product 76. (Gal $H_2O$ per 100 lbs. of Product 76) |
| | 200 Mesh = 1.04 Ml per gram (11.5 gal. $H_2O$ per 100 lb. of product) |
| | 325 Mesh = 1.84 Ml per gram (22 gals. $H_2O$ per 100 lb. of product) |
| | Fines = 44½ gal. $H_2O$ per 100 lbs. of product |
| PH-8.3 (20% of Water Slurry) | |

Synthetic domains can be prepared by employing the methods described in my prior U.S. Pat. No. 3,353,981, then subjecting the bonded material to mechanical size reduction to form the domains for further use in accordance with the techniques of the present invention. FIGS. 9 and 10 show a synthetic domain in which are dispersed hollow glass microspheres 12 and synthetic plastic matrix 18.

The preferred material, however, is the naturally occurring rhyolitic tuff previously described, and in each of the above examples "microspheres" actually refers to the domain aggregate of microspheres shown in the accompanying drawings.

While certain embodiments of the present invention have been shown and described herein, it is to be understood that changes and additions may be made by those skilled in the art without departing from the scope and spirit of the invention.

What is claimed is:

1. A microporous plastic composition comprising a synthetic resin matrix and a network of domains dispersed throughout said matrix; each of said domains comprised of plurality of porous microspheres bonded together with a bonding agent that is insoluble in the synthetic resin matrix; said composition having a relatively uniform gas permeability.

2. A microporous plastic composition comprising a synthetic resin matrix and a network of contiguous domains dispersed throughout said matrix; each of said domains comprised of a plurality of discrete porous microspheres bonded together with a bonding agent that is insoluble in the synthetic resin matrix.

3. The composition according to claim 1, wherein said domains are comprised of vitreous rhyolitic tuff.

4. The composition according to claim 1, wherein said domain is comprised of glass microspheres bonded together by a polymerized resin.

5. The composition according to claim 4, wherein said polymerized resin is polyvinylalcohol.

6. The composition according to claim 1, wherein said synthetic resin matrix is selected from the group consisting of phenol-formaldehyde, polysulfone, resorcinol-formaldehyde and polyvinylchloride; and wherein said domain is selected from the group consisting of vitreous rhyolitic tuff and glass microspheres bonded together with polyvinyl alcohol.

7. The composition according to claim 1, wherein said synthetic resin matrix is a thermosetting heat resistant resin and said domain is comprised of vitreous rhyolitic tuff.

8. A coated fabric comprising, in combination, a fabric layer, a flexible coating adhering to said fabric layer comprised of a synthetic resin matrix and a network of domains dispersed throughout said synthetic resin matrix; each of said domains comprised of a plurality of microspheres bonded together with a bonding agent which is insoluble in said synthetic resin matrix.

9. The coated fabric according to claim 8, wherein synthetic resin matrix is polyvinylchloride and said domain is comprised of vitreous rhyolitic tuff.

10. The coated fabric according to claim 8, wherein said fabric layer is comprised of a fabric selected from the group consisting of non-woven polyester fabrics and nylon duck.

* * * * *